United States Patent
Bhuiya et al.

(10) Patent No.: US 10,370,683 B2
(45) Date of Patent: Aug. 6, 2019

(54) METHODS OF USING O-METHYLTRANSFERASE FOR BIOSYNTHETIC PRODUCTION OF PTEROSTILBENE

(71) Applicant: CONAGEN INC., Bedford, MA (US)

(72) Inventors: Mohammad Wadud Bhuiya, Saint Louis, MO (US); Yechun Wang, Saint Louis, MO (US); Xiaodan Yu, Lexington, MA (US)

(73) Assignee: Conagen Inc., Bedford, MA (US)

( * ) Notice: Subject to any disclaimer, the term of this patent is extended or adjusted under 35 U.S.C. 154(b) by 196 days.

(21) Appl. No.: 15/033,705

(22) PCT Filed: Nov. 3, 2014

(86) PCT No.: PCT/US2014/063682
§ 371 (c)(1),
(2) Date: May 2, 2016

(87) PCT Pub. No.: WO2015/066609
PCT Pub. Date: May 7, 2015

(65) Prior Publication Data
US 2016/0273006 A1    Sep. 22, 2016

Related U.S. Application Data

(60) Provisional application No. 61/898,899, filed on Nov. 1, 2013.

(51) Int. Cl.
*C12P 7/22* (2006.01)
*C12N 9/10* (2006.01)
*C12N 9/00* (2006.01)

(52) U.S. Cl.
CPC ............. *C12P 7/22* (2013.01); *C12N 9/1007* (2013.01); *C12N 9/1029* (2013.01); *C12N 9/93* (2013.01); *C12Y 203/01095* (2013.01); *C12Y 602/01012* (2013.01)

(58) Field of Classification Search
CPC ....... C12N 9/1107; C12N 9/1029; C12N 9/93
See application file for complete search history.

(56) References Cited

U.S. PATENT DOCUMENTS 6,020,129 A    2/2000   Schroder et al.
2016/0215306 A1*  7/2016  Baerends ............. C12Y 201/00

FOREIGN PATENT DOCUMENTS

| CN | 102120996 A | 7/2011 |
| CN | 103773704 B | 10/2015 |
| KR | 2014-0040372 A | 4/2014 |
| WO | WO 2006/089898 A1 | 8/2006 |
| WO | WO 2008/009728 A1 | 1/2008 |
| WO | WO 2009/124966 A2 | 10/2009 |

OTHER PUBLICATIONS

Zhang & Yu, DQ366301, Vitis vinifera resveratrol synthase (STS1) mRNA, Feb. 2006. Retrieved from < https://www.ebi.ac.uk/ena/data/view/DQ366301 >.*
Lee et al., "The *Arabidopsis thaliana* 4-coumarate:CoA ligase (4CL) gene: stress and developmentally regulated expression and nucleotide sequence of its cDNA", Plant Molecular Biology, 1995, vol. 28, pp. 871-884.*
International Search Report and Written Opinion corresponding to International Patent Application No. PCT/US2014/63682, dated Jan. 27, 2015.
Zhang et al, Using Unnatural Protein Fusions to Engineer Resveratrol Biosynthesis in Yeast and mammalian Cells, J Am Chem Soc. Oct. 2006, vol. 128, No. 40, p. 13030-13031.
Schmidlin et al., A stress-inducible resveratrol O-methyltransferase involved in the biosynthesis of pterostilbene in grapevine. Plant Physiol, Nov. 2008, vol. 148, No. 3, p. 1630-1639.
Wang et al., Pterostilbene production by microorganisms expressing resvetrol O-methyltransferase. Ann. Microbiol. Jun. 2014, ISSN 1869-2044, p. 7, col. 1, para 1.
Watts et al., Biosynthesis of plant-specific stilbene polyketides in metabolically engineered *Escherichia coli*. BMC Biotechnol. Mar. 21, 2006;6:22.
[No Author Listed] Production of functional stilbene compounds with anti-viral KRIBB. Nov. 26, 2010.
EP 14858679.5, Feb. 22, 2017, Extended European Search Report.

* cited by examiner

*Primary Examiner* — Suzanne M Noakes
(74) *Attorney, Agent, or Firm* — Wolf, Greenfield & Sacks, P.C.; Karen K. Chan

(57) ABSTRACT

A biosynthetic method of making pterostilbene including expressing a 4-coumaratexoenzyme A ligase (4CL) in a cellular system, expressing a stilbene synthase (STS) in the cellular system, expressing a resveratrol O-methyltransferase (ROMT) in the cellular system, feeding p-coumaric acid to the cellular system, growing the cellular system in a medium, and producing pterostilbene.

13 Claims, 10 Drawing Sheets

Specification includes a Sequence Listing.

METHODS OF USING O-METHYLTRANSFERASE FOR BIOSYNTHETIC PRODUCTION OF PTEROSTILBENE

CROSS-REFERENCE TO RELATED APPLICATIONS

This disclosure is a PCT Patent application entitled Method of Using O-methyltransferase for Biosynthetic Production of Pterostilbene. This application claims priority to U.S. Provisional Patent application No. 61/898,899 filed on Nov. 1, 2013, which is incorporated by reference herein in its entirety.

TECHNICAL FIELD

This disclosure has applicability in the food, medicinal, and pharmacological industries. This disclosure relates generally to methods for the biosynthetic production of pterostilbene utilizing O-methyltransferase (ROMT).

BACKGROUND OF THE DISCLOSURE

Background Art

Pterostilbene is a stilbenoid chemically related to resveratrol and is found in blueberries and grapes. It belongs to the group of phytoalexins, agents produced by plants to fight infections. Based on animal studies, it is thought to exhibit anti-cancer, anti-hypercholesterolemia, anti-hypertriglyceridemia properties, as well as the ability to fight off and reverse cognitive decline. It is believed that the compound also has anti-diabetic properties, but so far very little has been studied on this issue.

Schmidlin et al. have reported that resveratrol O-methyltransferase (ROMT) could catalyze the direct conversion of resveratrol into pterostilbene (Schmidli et al., 2008). (Accession No: FM178870). Pterostilbene is produced by the action of 4-coumarate-CoA ligase (4CL), stilbene synthase (STS) and resveratrol O-methyltransferase (ROMT) (FIG. 1).

In this invention, Applicants demonstrate that ROMT can be expressed in a cellular system along with 4CL and STS to convert resveratrol into pterostilbene.

BRIEF SUMMARY OF DISCLOSURE

The disclosure addresses the technical issue of producing pterostilbene in a cellular system, such as yeast or bacteria. Applicants have uniquely isolated the genes for 4-coumarate:coenzyme A ligase (4CL), stilbene synthase (STS), and resveratrol O-methyltransferase (ROMT) and expressed them in a cellular system that facilitate the production of pterostilbene. This disclosure provides for the industrial production of resveratrol and pterostilbene.

The present disclosure is a biosynthetic method of making pterostilbene comprising expressing a 4-coumarate:coenzyme A ligase (4CL) in a cellular system, expressing a stilbene synthase (STS) in the cellular system, expressing a resveratrol O-methyltransferase (ROMT) in the cellular system, feeding p-coumaric acid to the cellular system, growing the cellular system in a medium, and thereby, producing pterostilbene.

Another embodiment is a biosynthetic method of making pterostilbene comprising expressing a resveratrol O-methyltransferase (ROMT) in the cellular system, feeding resveratrol to the cellular system, growing the cellular system in a medium, and producing pterostilbene.

Another embodiment is a biosynthetic method of making resveratrol comprising expressing a 4-coumarate:coenzyme A ligase (4CL) in a cellular system, expressing a stilbene synthase (STS) in the cellular system, feeding p-coumaric acid to the cellular system, growing the cellular system in a medium, and producing resveratrol.

Another embodiment is a biosynthetic method of making pterostilbene comprising expressing a 4-coumarate:coenzyme A ligase (4CL) in a first cellular system, expressing a stilbene synthase (STS) in the first cellular system, feeding p-coumaric acid to the first cellular system, growing the first cellular system in a medium, producing resveratrol, expressing a resveratrol O-methyltransferase (ROMT) in a second cellular system, feeding the produced resveratrol to the second cellular system, growing the second cellular system in a medium, and producing pterostilbene.

BRIEF DESCRIPTION OF THE DRAWINGS

For a better understanding of the present disclosure, reference may be made to the accompanying drawings in which.

Figure 1:
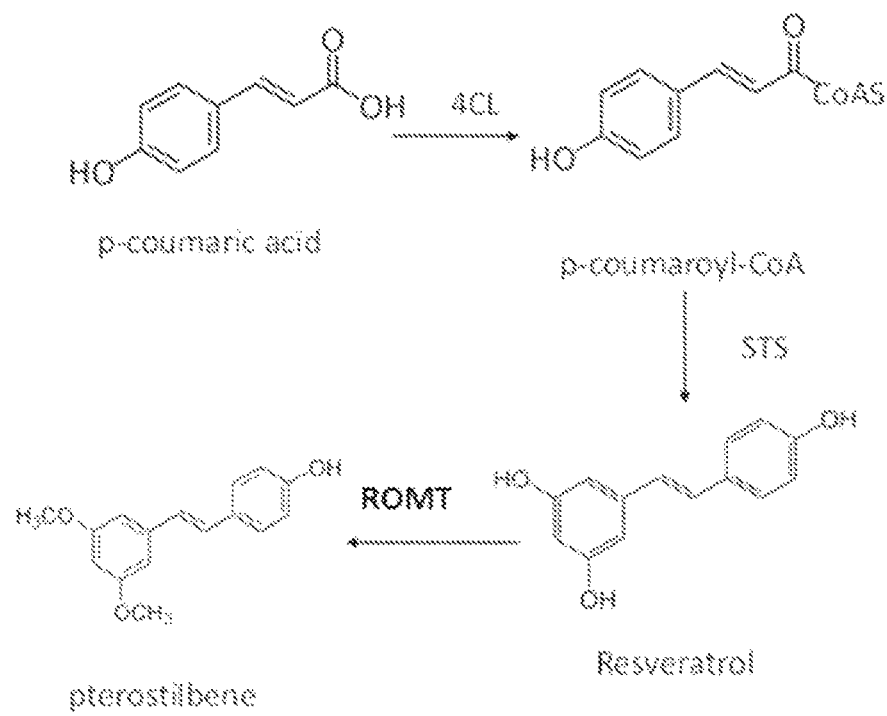
FIG. 1 shows the biosynthetic pathway of pterostilbene.

While the disclosure is susceptible to various modifications and alternative forms, specific embodiments thereof are shown by way of example in the drawing and will herein be described in detail. It should be understood, however, that the drawings and detailed description presented herein are not intended to limit the disclosure to the particular embodiment disclosed, but on the contrary, the intention is to cover all modifications, equivalents, and alternatives falling within the spirit and scope of the present disclosure as defined by the appended claims.

DETAILED DESCRIPTIONS OF THE DISCLOSURE

Definition

Cellular System

Cellular system is any cells that provide for the expression of ectopic proteins. It included bacteria, yeast, plant cells and animal cells. It includes both prokaryotic and eukaryotic cells. It also includes the in vitro expression of proteins based on cellular components, such as ribosomes.

Growing the Cellular System

Growing includes providing medium that would allow cells to multiply and divide. It also includes providing resources so that cells or cellular components can translate and make recombinant proteins.

Transfection

Transfection is the process of deliberately introducing nucleic acids into cells. The term is often used for non-viral methods in eukaryotic cells. It may also refer to other methods and cell types, although other terms are preferred: "transformation" is more often used to describe non-viral DNA transfer in bacteria, non-animal eukaryotic cells, including plant cells. In animal cells, transfection is the preferred term as transformation is also used to refer to progression to a cancerous state (carcinogenesis) in these cells. Transduction is often used to describe virus-mediated DNA transfer. Transformation, transduction, and viral infection are included under the definition of transfection for this application.

Modified Amino Acid

A modified amino acid is one that has been chemically modified and it can be incorporated as part of a polypeptide sequence. The amino acid could be modified in a post-translational manner or prior to incorporation in the polypeptide sequence during translation.

4CL

The 4-coumarate:coenzyme A ligase is expressed from a 4CL gene cloned from Arabidopsis thaliana (ecotype Columbia-0). In another embodiment, the 4-coumarate:coenzyme A ligase is expressed from a gene that has a sequence identity of at least 66% with a 4CL gene cloned from Arabidopsis thaliana (ecotype Columbia-0). In a further embodiment, the 4-coumarate:coenzyme A ligase is expressed from a gene that has a sequence similarity of at least 90% with a 4CL gene cloned from Arabidopsis thaliana (ecotype Columbia-0).

STS

The stilbene synthase is expressed from a STS gene cloned from grape (Vitis vinifera). In another embodiment, the stilbene synthase is expressed from a gene that has a sequence identity of at least 66% with a STS gene cloned from grape (Vitis vinifera). In a further embodiment, the stilbene synthase is expressed from a gene that has a sequence similarity of at least 90% with a STS gene cloned from grape (Vitis vinifera).

ROMT

The resveratrol O-methyltransferase is expressed from a gene cloned from grape (Vitis vinifera). In another embodiment, the resveratrol O-methyltransferase is expressed from a gene that has a sequence identity of at least 66% with a ROMT gene cloned from grape (Vitis vinifera). In a further embodiment, the resveratrol O-methyltransferase is expressed from a gene that has a sequence similarity of at least 90% with a ROMT gene cloned from grape (Vitis vinifera).

An embodiment of the present disclosure is a biosynthetic method of making pterostilbene including expressing a 4-coumarate:coenzyme A ligase (4CL) in a cellular system, expressing a stilbene synthase (STS) in the cellular system, expressing a resveratrol O-methyltransferase (ROMT) in the cellular system, feeding p-coumaric acid to the cellular system, growing the cellular system in a medium, and producing pterostilbene.

In one embodiment, expressing the 4-coumarate:coenzyme A ligase and expressing the stilbene synthase comprise transfecting a 4CL::STS fusion gene. In another embodiment, expressing the 4-coumarate:coenzyme A ligase comprises transfecting a 4CL gene and expressing the stilbene synthase comprises transfecting a separate STS gene. Expressing the resveratrol O-methyltransferase comprises transfecting a ROMT gene.

The cellular system is selected from the group consisting of at least, bacteria, yeast, and a combination thereof. In another embodiment, the cellular system allows for ectopic biosynthetic reaction.

A further embodiment is a biosynthetic method of making pterostilbene comprising expressing a resveratrol O-methyltransferase (ROMT) in the cellular system, feeding resveratrol to the cellular system, growing the cellular system in a medium, and producing pterostilbene.

A further embodiment is a biosynthetic method of making resveratrol comprising expressing a 4-coumarate:coenzyme A ligase (4CL) in a cellular system, expressing a stilbene synthase (STS) in the cellular system, feeding p-coumaric acid to the cellular system, growing the cellular system in a medium, and producing resveratrol.

A further embodiment is a biosynthetic method of making pterostilbene comprising expressing a 4-coumarate:coenzyme A ligase (4CL) in a first cellular system, expressing a stilbene synthase (STS) in the first cellular system, feeding p-coumaric acid to the first cellular system, growing the first cellular system in a medium, producing resveratrol, expressing a resveratrol O-methyltransferase (ROMT) in a second cellular system, feeding resveratrol to the second cellular system, growing the second cellular system in a medium, and producing pterostilbene.

Materials and Methods

Strains, Plasmids and Culture Condition

HI-Control 10G and DH5a were used for plasmid cloning, and BL21 (DE3) (Invitrogen) was used for recombinant protein expression in E. coli. Wat11 strain was used for protein expression in yeast. p-Coumaric acid, resveratrol and pterostilbene standard were all purchased from Sigma. The pETite N-His SUMO Kan Vector were purchased from Lucigen (Middleton, Wis.). Plasmid pETDuet-1 were purchased from Novagen was used recombinant protein expression purposes.

DNA Manipulation

All DNA manipulations were performed according to standard procedures. Restriction enzymes and T4 DNA Ligase were purchased from New England Biolabs. All PCR amplification and cloning reactions were performed using Phusion® High-Fidelity DNA Polymerase New England Biolabs.

RNA Extraction and cDNA Synthesis

ROMT (resveratrol O-methyltransferase), 4CL (4-coumarate:coenzyme A ligase) and STS (stilbene synthase) were cloned from various plant species. Plant total RNA was extracted from grape (Vitis vinifera) for the cloning of ROMT and STS and Arabidopsis thaliana (ecotype Columbia-0) for the cloning of 4CL with Trizol Plus RNA Purification Kit (Invitrogen Inc). The synthesis of cDNA was carried out with Im Prom-II™ Reverse Transcription System from Promega Inc. following the manufacturer's manual. The genes were amplified from the synthesized cDNA with New England Biolabs Phusion PCR Kit with the primers listed in Table 1.

Example 1

Construction of Bacterial Expression Vector

The PCR product of ROMT was cloned into pETite N-His SUMO Kan Vector (Lucigen Inc) according to the manufacturer's manual. The resultant plasmid with the right insert was confirmed by sequencing, namely Sumo-ROMT, and was transformed into BL21(DE3) for heterogeneous gene expression.

To construct the 4CL::STS fusion gene, At4CL and VvSTS were fused using the PCR amplification strategy. The stop codon of 4CL was removed and a three amino acid linker (Gly-Ser-Gly) was introduced between the open reading frame of 4CL and STS. This construction resulted in a 2.87 kb fused gene construct encoding 4CL, the tripeptide linker, and STS. The fusion gene 4CL::STS cloned into the Gateway entry vector using the pCR8/GW/TOPO TA Cloning kit (Invitrogen), was transformed into One Shot E. coli cells, and then sequenced. 4CL::STS fusion gene was amplified and cloned into the multiple cloning site of pETDuet-1 vector via BamHI/HindIII, name pETDuet-4CLSTS. Primers for all cloning reactions are available in the Table 1.

Example 2

Construction of Yeast Expression Vector

The 4CL::STS gene was introduced into the S. cerevisiae Advanced Gateway destination vector pAG304GPD-ccdB (Addgene, Boston, Mass.), and the ROMT gene was swapped into another Gateway destination vector pAG305GPD-ccdB (Addgene) by LR clonase II enzyme mix kit (Invitrogen). The resultant plasmids were named pAG304GPD-4CLSTS and pAG304GPD-ROMT. The vectors contain integrative recombination side and an expression cassette under the control of a constitutive promoter (GPD). These vectors were transformed into WAT11 for fermentation assays.

Yeast Transformation

The constructs, pAG304GPD-4CLSTS and pAG304GPD-ROMT, along with the pAG304GPD-ccdB and pAG305GPD-ccdB vectors as controls, were transformed into WAT11 cells with the Frozen-EZ Yeast Transformation II kit (Zymo Research, Orange, Calif.). Vectors, pAG304GPD-4CLSTS and pAG304GPD-ROMT, were cotranformed into yeast WAT11 cells.

Figure 9:
FIG. 9 shows model of ROMT represented by ribbon. Substrates are represented by stick model in dark gray. Substrate binding residues are represented by stick model in black color. F167A, D174A, W258A, H261A (H261 is key amino acid) are changes made. They are all key amino acids for activity with H261 being the most important.

Homology Modeling and Docking for Prediction of Substrate Binding Residues of ROMT According to applicants' knowledge, there is no tertiary structure of ROMT that can be used for analyses of substrate binding sites. To analyze the substrate binding site, applicants built a model for ROMT (FIG. 9) with a computer program I-TASSER (Ambrish et al., 2010). Applicants apply a combined method of molecular biology and structural biology for the laboratory evolution and development of enhanced ROMT. The substrate binding site was predicted by docking resveratrol with the ROMT model using the computer program SWISDOCK (Grosdidier et al., 2011).

The Bioconversion of P-Coumaric Acid to Resveratrol with the Protein of 4CL::STS Fusion Protein in E. coli and S. cerevisiae Single colony of the E. coli strain was grown in 3 mL LB medium with 100 μg/mL ampicillin overnight at 37° C., and then the seed culture was transferred to 50 mL M9 modified medium with 100 μg/mL ampicillin. E.coli BL21(DE3) containing pETDuet-4CLSTS vector was kept shaking at 200 rpm at 37° C. in modified M9 medium until OD600 reach to 0.6, then added 1 mM IPTG, after 2 hour induction with IPTG, p-coumaric acid was dissolved in 100% ethanol was added to the culture to 0.5 g/L. The culture was kept shaking under the same culture condition, and samples were taken at interval for HPLC analysis.

Wat11 cells containing pAG304GPD-4CLSTS plasmid were grown in SD drop out medium at 30° C. until OD600 reach to 0.2, then add p-coumaric acid (0.5 g/L). The culture was kept shaking for 4 days under the same culture condition, and samples were taken at interval for HPLC analysis.

The Bioconversion of Resveratrol to Pterostilbene with the Protein of ROMT in E.coli and S. cerevisiae E.coli BL21(DE3) containing SUMO-RMOT vector was grown in modified M9 medium at 37° C. until OD600 reach to 0.6, then add 1 mM IPTG, after 2 hour induction with IPTG, resveratrol dissolved in DMSO was added to the culture to 0.228 g/L. M9 medium was modified by addition of yeast extract (1.25 g/L) and glycerol (0.5% v/v) into standard M9 medium. The culture was kept shaking under the same culture condition, and samples were taken at interval for HPLC analysis.

Wat11 cells containing pAG305GPD-RMOT plasmid were grown in standard yeast drop-out medium at 30° C. until OD600 reach to 0.2, then add resveratrol acid (0.228 g/L). The culture was kept shaking under the same culture condition, and samples were taken at interval for HPLC analysis.

The Bioconversion of P-Coumaric Acid to Pterostilbene with the Protein of ROMT and 4CL::STS Fusion Protein in E.coli and S. cerevisiae E. coli BL21(DE3) containing pETDuet-4CLSTS and SUMO-ROMT vectors was grown in modified M9 medium at 37° C. until OD600 reach to 0.6, then add 1 mM IPTG, after 2 hour induction with IPTG, p-coumaric acid dissolved in 100% ethanol was added to the culture to 0.5 g/L. The culture was kept shaking under the same culture condition, and samples were taken at interval for HPLC analysis.

Wat11 cells containing pAG304GPD-4CLSTS and pAG305GPD-ROMT plasmid were grown in SD drop out medium at 30° C. until OD600 reach to 0.2, then add p-coumaric acid (0.5 g/L). The culture was kept shaking under the same culture condition, and samples were taken at interval for HPLC analysis.

Extraction of Products

Aliquots of cultures (400 ul) were extracted with 800 ul of ethyl acetate. Extracts were evaporated to dryness with an Eppendorf Vacufuge (Eppendorf Scientific Westbury, N.Y.) at room temperature and re-dissolved in 200 ul of 80% (v/v) methanol.

HPLC Analysis.

The HPLC analysis of resveratrol and pterostilbene was carried out with Dionex Ultimate 3000 system. Intermediates were separated by reverse-phase chromatography on a phenomenex Kinetex C18 column (particle size 2.6 μm; 150×4.6 mm) with 0.1% (vol/vol) formic acid (Solution A) and 100% acetonitrile (Solution B). Samples were diluted into 80% methanol, and the following gradient procedure was used: 10% of solution B for 2 min; a linear gradient from 10% to 70% of solution B for 18 min; from 70% to 30% of solution B for 1 min; from 30% to 10% of solution B for 2 min; 10% of solution B for 5 min at a flow rate of 0.8 ml/min. For quantification, all intermediates were calibrated with external standards. The compounds were identified by their retention times, as well as the corresponding spectra, which were identified with a diode array detector in the system.

Figure 2:
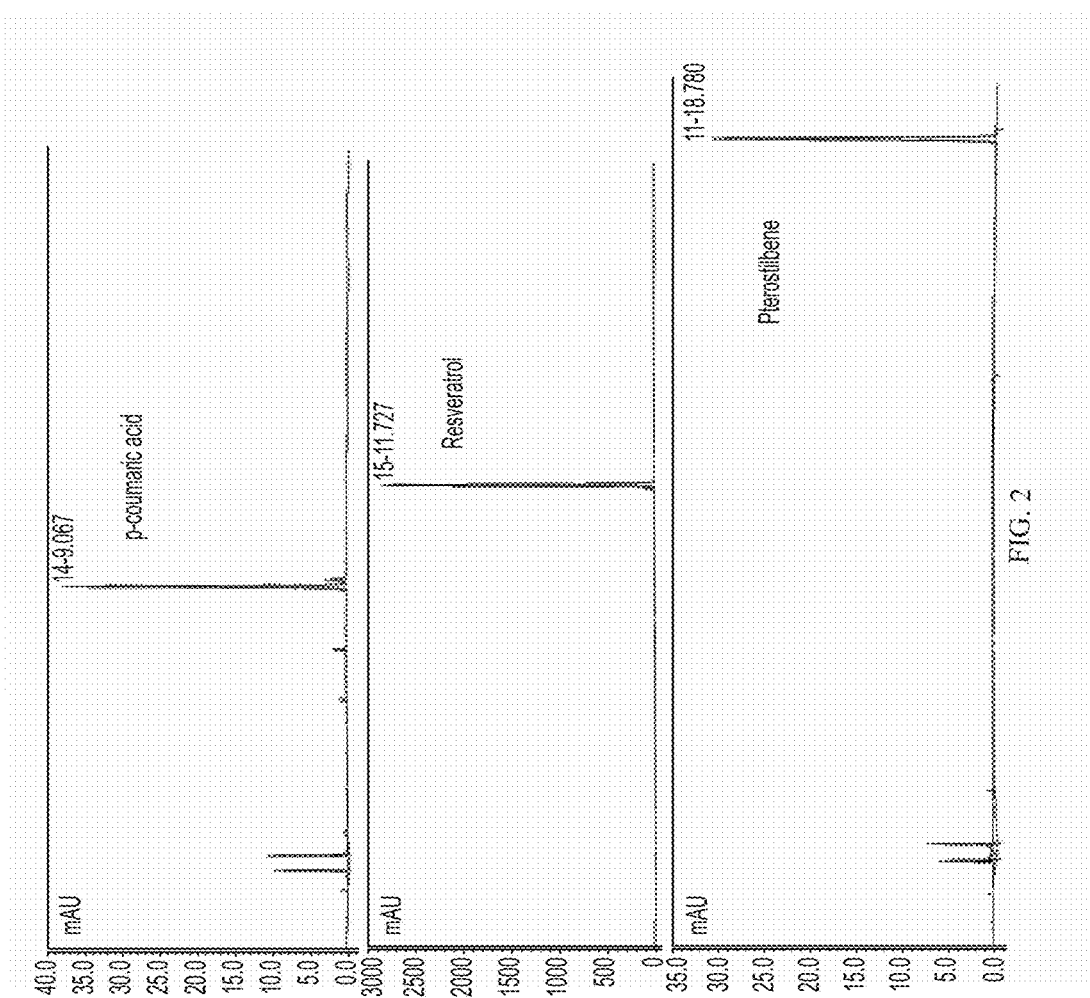
FIG. 2 shows HPLC profiles of three standards (p-coumaric acid, resveratrol and pterostilbene).
Figure 3:
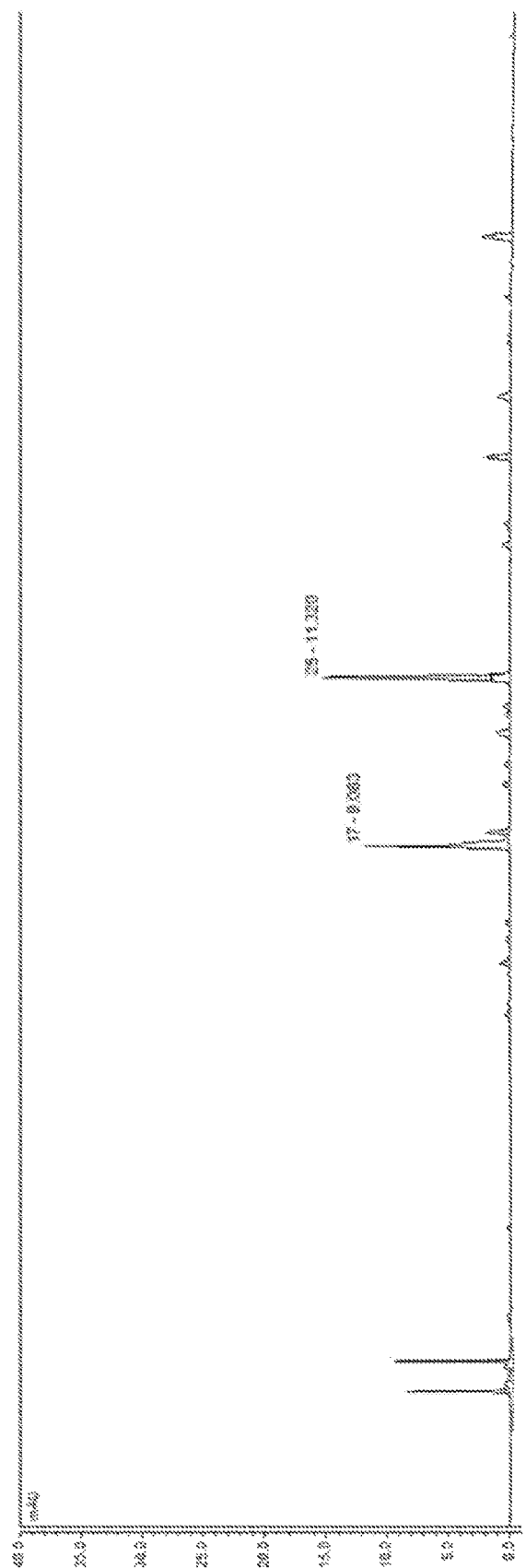
FIG. 3 shows HPLC profiles of extracts from *E. coli* cells expressing 4CL::STS fusion gene.

Results
The Bioconversion of P-Coumaric Acid to Resveratrol with Fusion Protein of 4CL and STS Three standards were run by HPLC, which shows that they were separated well (FIG. 2). With the PCR amplification strategy, 4CL and STS were fused with a link of Gly-Ser-Gly between 4CL and STS. Applicants tested the conversion of p-coumaric acid to resveratrol with the *E.coli* BL21(DE3) strain containing pETDuet-4CLSTS plasmid in modified M9 medium in the flasks. As shown in FIG. 3, p-coumaric acid could be converted into resveratrol in modified M9 medium.

Figure 6:
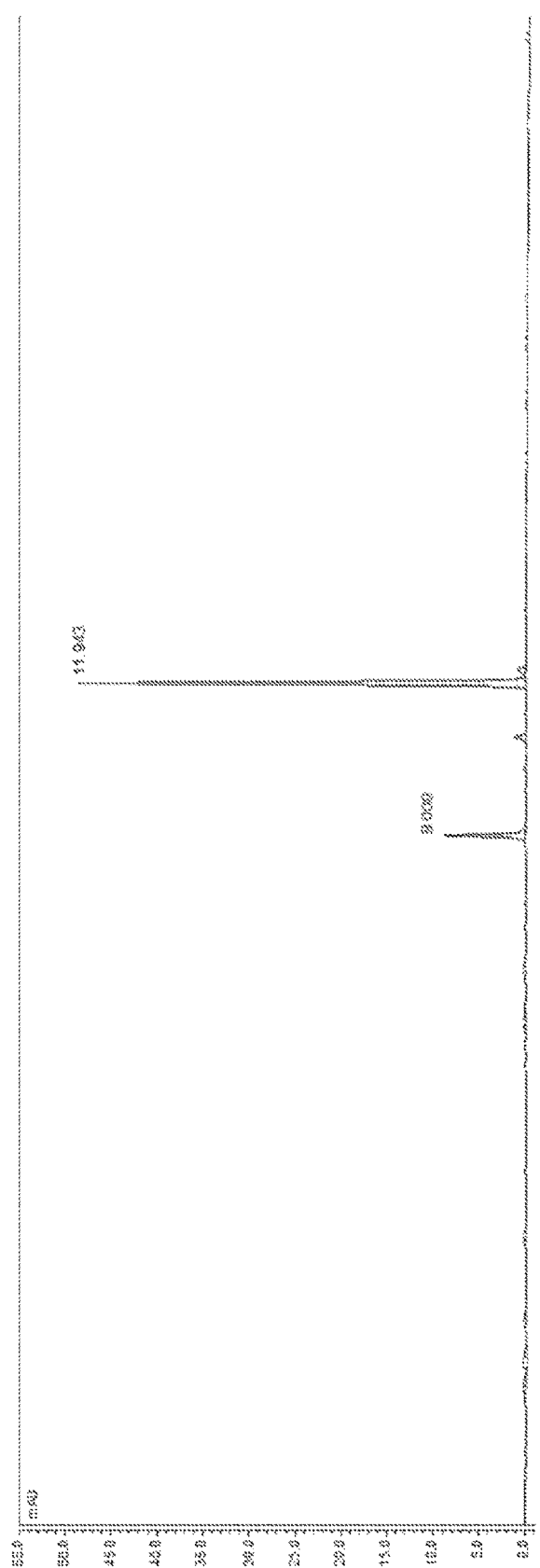
FIG. 6 shows HPLC profiles of extracts from yeast cells expressing 4CL::STS fusion gene.

For in vivo yeast assay, fresh yeast colonies containing pAG304GPD-4CLSTS were grown at 30° C. in 3 ml yeast drop out medium containing 0.5 g/L p-coumaric acid for 4 days. Extracts were analyzed by HPLC. As shown in FIG. 6, almost all p-coumaric acid was converted into resveratrol within 4 days. Compared with *E. coli*, the conversion efficiency in yeast was much better.

The Bioconversion of Resveratrol to Pterostilbene with the Protein of ROMT

Figure 4:
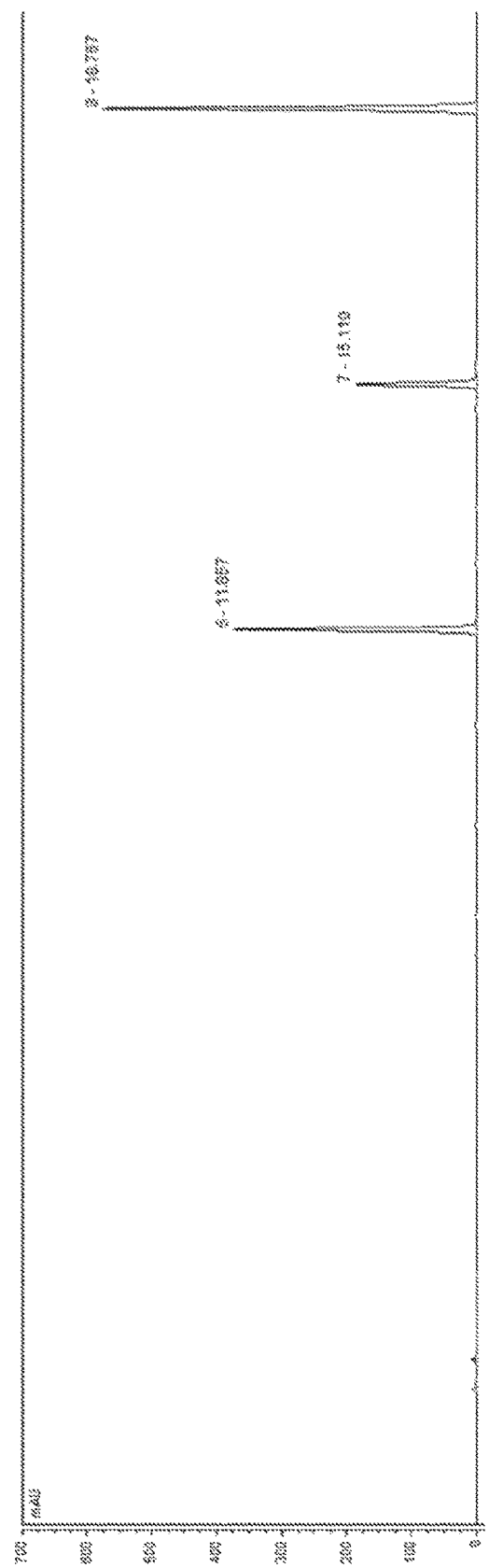
FIG. 4 shows HPLC profiles of extracts from *E. coli* cells expressing ROMT gene.
Figure 7:
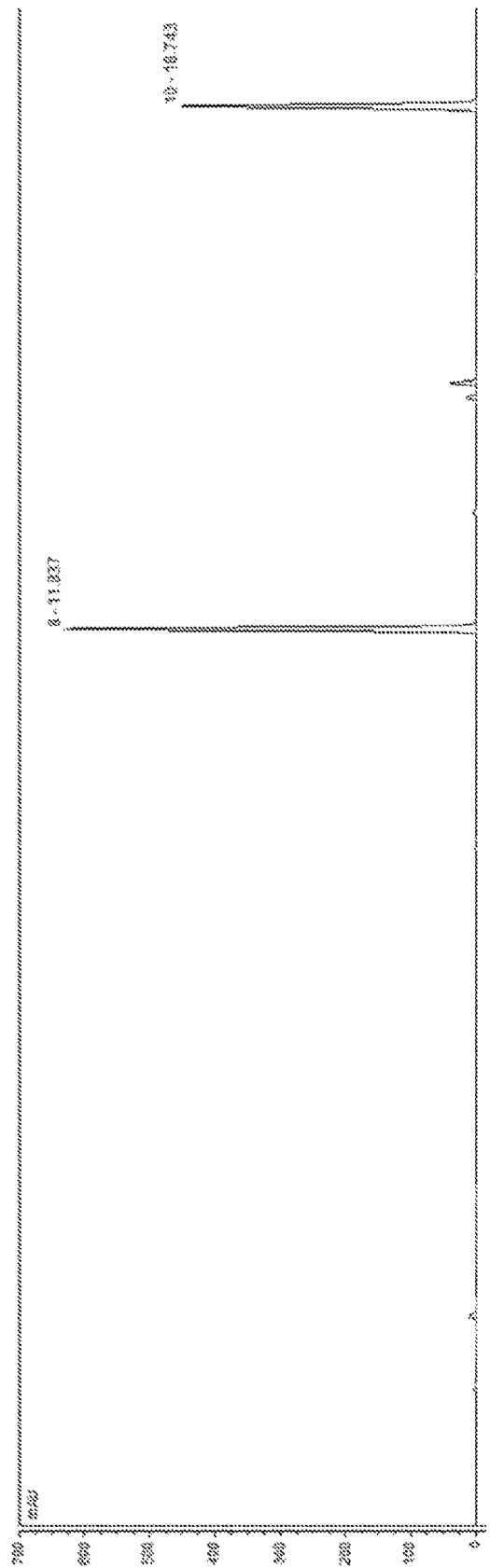
FIG. 7 shows HPLC profiles of extracts from yeast cells expressing ROMT gene.

As shown in FIG. 4, resveratrol fed into the culture of *E.coli* with the expression of ROMT was converted into pterostilbene in the flask. HPLC analysis indicates resveratrol can be converted into pterostilbene in flask. However, there is another unknown peak, which probably is that one of a methyl group added onto resveratrol. Similar results also were attained from yeast (FIG. 7).

Figure 5:
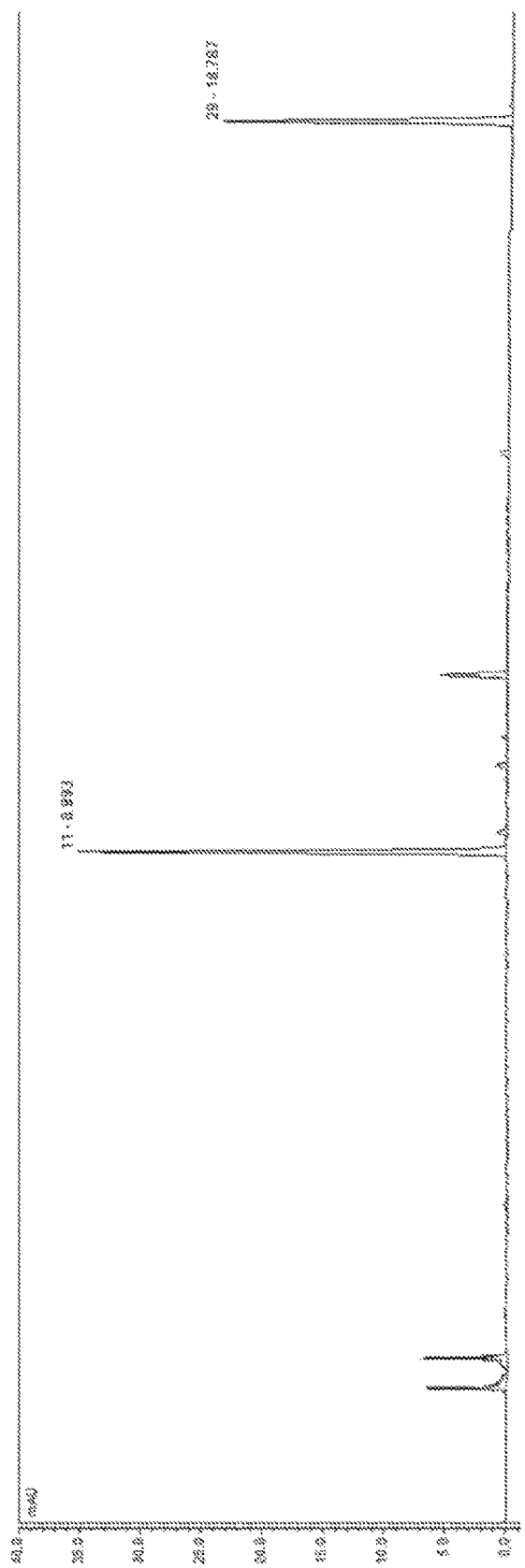
FIG. 5 shows HPLC profiles of extracts from *E. coli* cells co-expressing 4CL::STS and ROMT gene.
Figure 8:
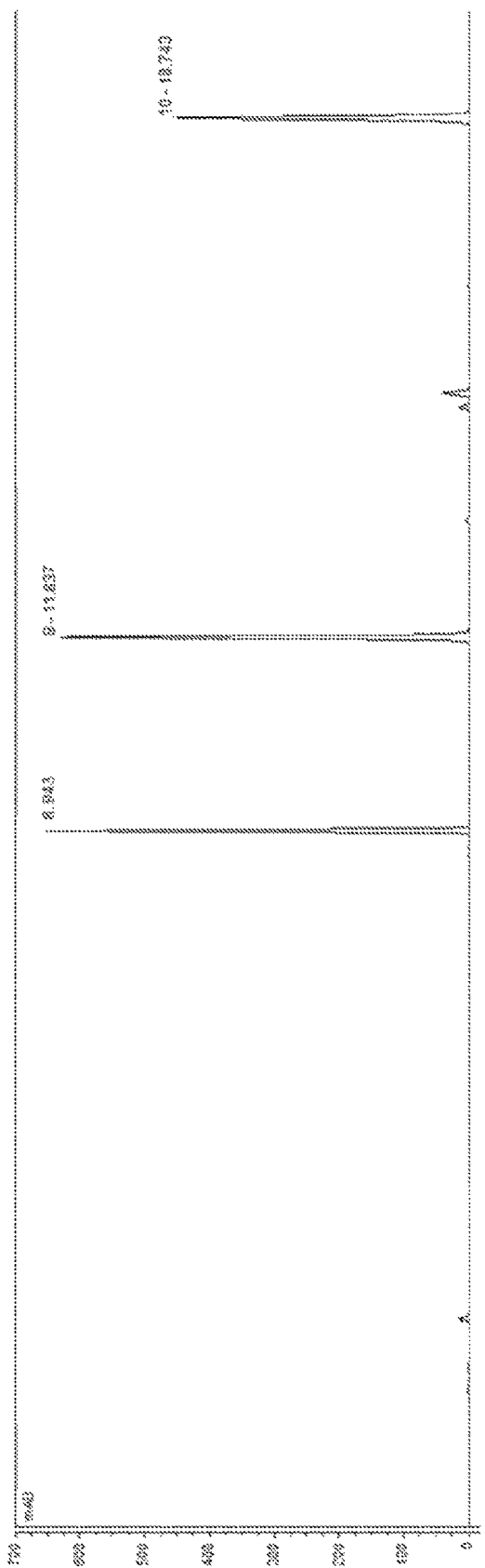
FIG. 8 shows HPLC profiles of extracts from yeast cells co-expressing 4CL::STS and ROMT gene.

The Bioconversion of P-Coumaric Acid to Pterostilbene with Co-Expression 4CL::STS and ROMT p-Coumaric acid was fed into the culture of *E.coli* and *S. cerevisiae* with the co-expression of 4CL::STS and ROMT, as shown in FIG. 5 and FIG. 8, p-coumaric acid was converted into resveratrol and pterostilbene in the flask by HPLC with 24 h in *E. coli* and *S. cerevisiae*. Profiles of HPLC were obtained under the condition within 96 hours.

Conventional and Saturation Mutagenesis of ROMT

Figure 10:
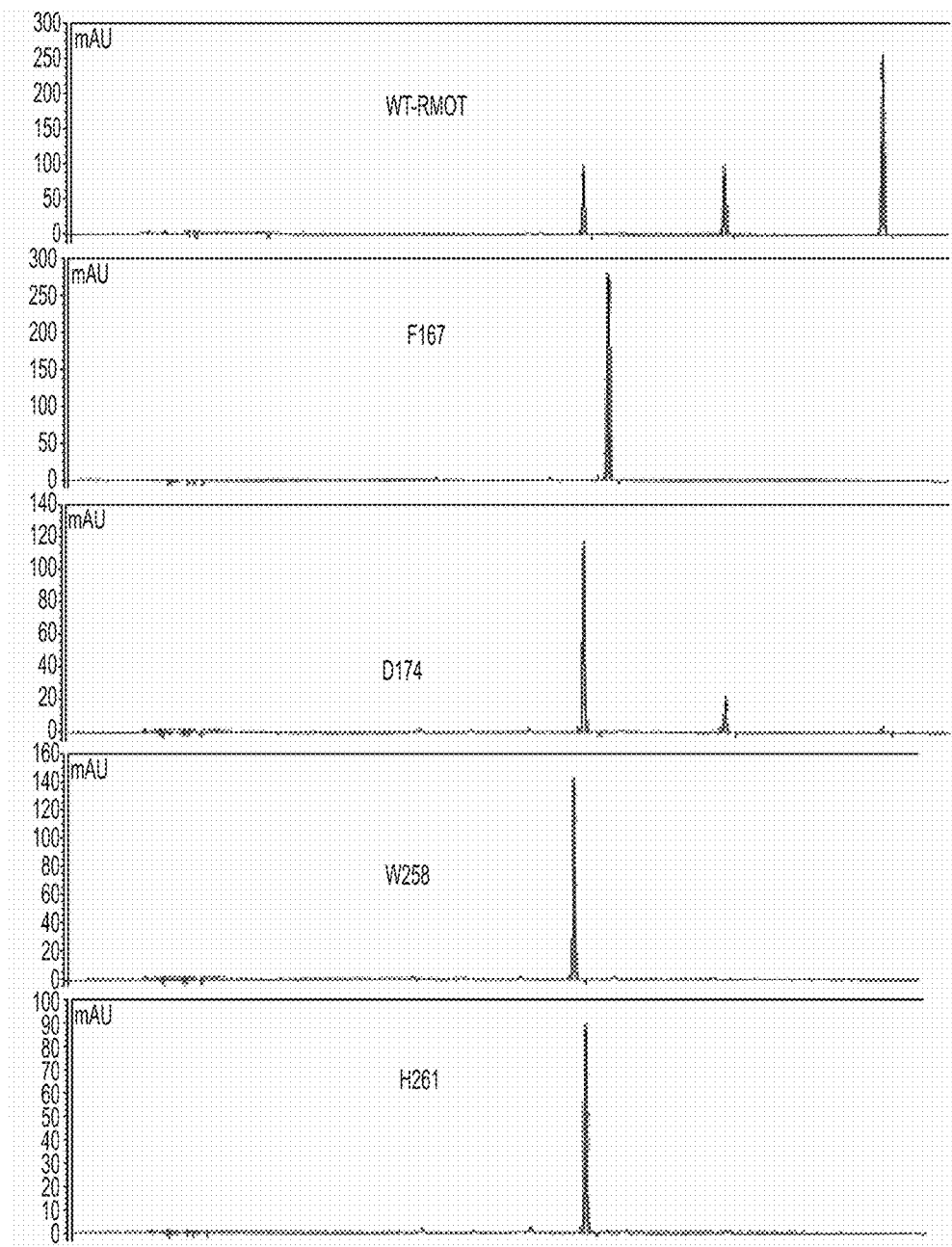
FIG. 10 shows HPLC profiles of extracts from *E. coli* cells expressing wild-type ROMT and ROMT-mutant.

After careful analysis of the substrate binding site, the amino acid residues 167, 174, 258, and 261 have been selected for saturation mutagenesis to improve the activity of ROMT. Applicants already performed conventional mutagenesis to construct F167A, D174A, W258A, and H261A mutants of ROMT to know their effect on enzyme activity. None of them show activity except D174A, which exhibited very low activity (FIG. 10). This result suggests that the amino acid residues at sites 167, 174, 258 and 261 are important for substrate binding and catalytic activity. Therefore, next step applicants will perform site-directed saturation mutagenesis to improve the enzymatic activity of ROMT. Saturation mutagenesis allow change one amino acid to other alternative 19 amino acid residues. Applicants will perform saturation mutagenesis at the site 167, 174, 258, and 261 of ROMT by following the modified Quick-Change site-directed mutagenesis strategy (Stratagene, Calif.) using NNK degenerate primers (N represents the mixture of A, T, G, C, and K for G/T). The codon NNK has 32-fold degeneracy and encodes all 20 amino acids without rare codons. The PCR mixture (25 µl) composed of Phusion HF buffer containing 60 ng Sumo-ROMT DNA template, 200 µM dNTPS, 0.5 µM forward primers, 0.5 µM reverse primers, 5% DMSO and 0.3 µl polymerase. The PCR was performed by denaturing at 98° C. for 20 sec, annealing at 58° C. for 30 sec and followed by elongation at 72° C. for 2 min 30 sec for 25 cycle. The QuikChange PCR products were examined by agarose gel electrophoresis and then 15 µl of PCR products were digested with 1 µl DpnI (New England Biolabs) at 37° C. for 4 hrs to remove the template plasmid. Aliquot of (2 µl) digestive products was added to 50 µl BL21(DE3) competent cells (Stratagene, Calif.), keep on ice for 30 min. After that, heat shock was done at 42° C. for 20 sec, keep on ice for 2 min and then 500 µl SOC medium was added and grow the cells at 37° C. for 1 hr. The cells were centrifuged at 5000 rpm for min, 450 µl supernatant was discarded and cells were suspended with the rest of the SOC medium and were inoculated on Luria-Bertani (LB) agar plates containing kanamycin (50 µg/ml). We will isolate the plasmid and DNA sequencing to confirm the mutant. We will confirm the quality of the library by DNA sequencing.

TABLE 1

Primers used in this study

| Name | Sequence (5'-3') |
|---|---|
| SumoROMTF | CGC GAA CAG ATT GGA GGT GAT TTG GCA AAC GGT GTG ATA TCA GC (SEQ ID NO: 1) |
| SumoROMTR | GTG GCG GCC GCT CTA TTA TCA AGG ATA AAC CTC AAT GAG GGA CC (SEQ ID NO: 2) |
| ROMTF | ATG GAT TTG GCA AAC GGT GTG ATA TC (SEQ ID NO: 3) |
| ROMTR | TCA AGG ATA AAC CTC AAT GAG GGA CC (SEQ ID NO: 4) |
| 4CL-F | ATG GCG CCA CAA GAA CAA GCA GTT TC (SEQ ID NO: 5) |
| 4CLSTS-LinkF | GAG GGC AAA ACT AGC AAA TGG ATT GGG ATC TGG CAT GGC TTC AGT CGA GGA ATT TAG AA (SEQ ID NO: 6) |
| 4CLSTS-LinkR | TTC TAA ATT CCT CGA CTG AAG CCA TGC CAG ATC CCA ATC CAT TTG CTA GTT TTG CCC TC (SEQ ID NO: 7) |
| STS-R | TTA ATT TGT AAC CAT AGG AAT GCT ATG (SEQ ID NO: 8) |
| 4CL-BamHIF | CGG GAT CCA TGG CGC CAC AAG AAC AAG CAG TTT C (SEQ ID NO: 9) |
| STS-HindIIIR | CCC AAG CTT TTA ATT TGT AAC CAT AGG AAT GCT ATG (SEQ ID NO: 10) |
| Oligo dT (22) | TTT TTT TTT TTT TTT TTT TTV N (SEQ ID NO: 11) |

Identity and Similarity

Identity is the fraction of amino acids that are the same between a pair of sequences after an alignment of the sequences (which can be done using only sequence information or structural information or some other information, but usually it is based on sequence information alone), and similarity is the score assigned based on an alignment using some similarity matrix. The similarity index can be any one of the following BLOSUM62, PAM250, or GONNET, or any matrix used by one skilled in the art for the sequence alignment of proteins.

Identity is the degree of correspondence between two sub-sequences (no gaps between the sequences). An identity of 25% or higher implies similarity of function, while 18-25% implies similarity of structure or function. Keep in mind that two completely unrelated or random sequences (that are greater than 100 residues) can have higher than 20% identity. Similarity is the degree of resemblance between two sequences when they are compared. This is dependent on their identity.

As is evident from the foregoing description, certain aspects of the present disclosure are not limited by the particular details of the examples illustrated herein, and it is therefore contemplated that other modifications and applications, or equivalents thereof, will occur to those skilled in the art. It is accordingly intended that the claims shall cover all such modifications and applications that do not depart from the spirit and scope of the present disclosure.

Moreover, unless defined otherwise, all technical and scientific terms used herein have the same meaning as commonly understood by one of ordinary skill in the art to which the disclosure belongs. Although any methods and materials similar to or equivalent to or those described herein can be used in the practice or testing of the present disclosure, the preferred methods and materials are described above.

Other aspects, objects and advantages of the present disclosure can be obtained from a study of the drawings, the disclosure and the appended claims.

REFERENCES

Schmidlin L, Poutaraud A, Claudel P, Mestre P, Prado E, Santos-Rosa M, Wiedemann-Merdinoglu S, Karst F, Merdinoglu D, Hugueney P (2008) A stress-inducible resveratrol O-methyltransferase involved in the biosynthesis of pterostilbene in grapevine. Plant Physiol. 148(3):1630-1639.

Ambrish R, Alper K, Yang Z (2010) I-TASSER: a unified platform for automated protein structure and function prediction. *Nature Protocols,* 5:725-738.

Grosdidier A, Zoete V, Michielin O. (2011) SwissDock, a protein-small molecule docking web service based on EADock DSS. Nucleic Acids Res. 39:W270-277.

---

What is claimed is:

1. A biosynthetic method of making pterostilbene comprising:
   expressing a 4-coumarate:coenzyme A ligase (4CL) in a cellular system;
   expressing a stilbene synthase (STS) in the cellular system;
   expressing a resveratrol O-methyltransferase (ROMT) in the cellular system;
   feeding p-coumaric acid to the cellular system;
   growing the cellular system in a medium; and
   producing pterostilbene,
   wherein the 4-coumarate:coenzyme A ligase is expressed from a gene that has a sequence identity of at least 66% with a 4CL gene comprising the sequence of SEQ ID NO: 14,
   wherein the stilbene synthase is expressed from a gene that has a sequence identity of at least 66% with a STS gene comprising the sequence of SEQ ID NO: 16,
   wherein the resveratrol O-methyltransferase is expressed from a gene that has a sequence identity of at least 66% with a ROMT gene comprising the sequence of SEQ ID NO: 12, and wherein the resveratrol O-methyltransferase expressed is modified at one or more residues in SEQ ID NO: 13 selected from the list consisting of residues 167, 174, 258, 261, and a combination thereof, by an alternative amino acid or a modified amino acid, and wherein the modified resveratrol O-methyltransferase exhibits increased activity in converting resveratrol to pterostilbene relative to an unmodified resveratrol O-methyltransferase comprising the sequence of SEQ ID NO: 13.

2. The biosynthetic method of making pterostilbene of claim 1, wherein the 4CL gene is cloned from *Arabidopsis thaliana*.

3. The biosynthetic method of making pterostilbene of claim 1, wherein the 4-coumarate:coenzyme A ligase is expressed from a gene that has a sequence similarity of at least 90% with a 4CL gene comprising the sequence of SEQ ID NO: 14.

4. The biosynthetic method of making pterostilbene of claim 1, wherein the STS gene is cloned from grape.

5. The biosynthetic method of making pterostilbene of claim 1, wherein the stilbene synthase is expressed from a gene that has a sequence similarity of at least 90% with a STS gene comprising the sequence of SEQ ID NO: 16.

6. The biosynthetic method of making pterostilbene of claim 1, wherein the resveratrol O-methyltransferase is expressed from a gene that has a sequence similarity of at least 90% with a ROMT gene comprising the sequence of SEQ ID NO: 12.

7. The biosynthetic method of making pterostilbene of claim 1, wherein the 4CL gene and the STS gene are a 4CL::STS fusion gene which is transfected.

8. The biosynthetic method of making pterostilbene of claim 1, wherein expressing the 4-coumarate:coenzyme A ligase comprises transfecting the 4CL gene.

9. The biosynthetic method of making pterostilbene of claim 1, wherein expressing the stilbene synthase comprises transfecting the STS gene.

10. The biosynthetic method of making pterostilbene of claim 1, wherein expressing the resveratrol O-methyltransferase comprises transfecting the ROMT gene which is modified.

11. The biosynthetic method of making pterostilbene of claim 1, wherein the cellular system is selected from the group consisting of bacteria, yeast, plant cells, animal cells and a combination thereof.

12. The biosynthetic method of making pterostilbene of claim 1, wherein the cellular system allows for ectopic biosynthetic reaction.

13. The biosynthetic method of making pterostilbene of claim 1, wherein the cellular system comprises an in vitro translation system.

* * * * *

SEQUENCE LISTING

<160> NUMBER OF SEQ ID NOS: 19

<210> SEQ ID NO 1
<211> LENGTH: 44
<212> TYPE: DNA
<213> ORGANISM: Artificial Sequence
<220> FEATURE:
<223> OTHER INFORMATION: Primer

<400> SEQUENCE: 1
cgcgaacaga ttggaggtga tttggcaaac ggtgtgatat cagc                44

<210> SEQ ID NO 2
<211> LENGTH: 44
<212> TYPE: DNA
<213> ORGANISM: Artificial Sequence
<220> FEATURE:
<223> OTHER INFORMATION: Primer

<400> SEQUENCE: 2
gtggcggccg ctctattatc aaggataaac ctcaatgagg gacc                44

<210> SEQ ID NO 3
<211> LENGTH: 26
<212> TYPE: DNA
<213> ORGANISM: Artificial Sequence
<220> FEATURE:
<223> OTHER INFORMATION: Primer

<400> SEQUENCE: 3
atggatttgg caaacggtgt gatatc                                    26

<210> SEQ ID NO 4
<211> LENGTH: 26
<212> TYPE: DNA
<213> ORGANISM: Artificial Sequence
<220> FEATURE:
<223> OTHER INFORMATION: Primer

<400> SEQUENCE: 4
tcaaggataa acctcaatga gggacc                                    26

<210> SEQ ID NO 5
<211> LENGTH: 26
<212> TYPE: DNA

```
<213> ORGANISM: Artificial Sequence
<220> FEATURE:
<223> OTHER INFORMATION: Primer

<400> SEQUENCE: 5
atggcgccac aagaacaagc agtttc                                       26

<210> SEQ ID NO 6
<211> LENGTH: 59
<212> TYPE: DNA
<213> ORGANISM: Artificial Sequence
<220> FEATURE:
<223> OTHER INFORMATION: Primer

<400> SEQUENCE: 6
gagggcaaaa ctagcaaatg gattgggatc tggcatggct tcagtcgagg aatttagaa   59

<210> SEQ ID NO 7
<211> LENGTH: 59
<212> TYPE: DNA
<213> ORGANISM: Artificial Sequence
<220> FEATURE:
<223> OTHER INFORMATION: Primer

<400> SEQUENCE: 7
ttctaaattc ctcgactgaa gccatgccag atcccaatcc atttgctagt tttgccctc   59

<210> SEQ ID NO 8
<211> LENGTH: 27
<212> TYPE: DNA
<213> ORGANISM: Artificial Sequence
<220> FEATURE:
<223> OTHER INFORMATION: Primer

<400> SEQUENCE: 8
ttaatttgta accataggaa tgctatg                                      27

<210> SEQ ID NO 9
<211> LENGTH: 34
<212> TYPE: DNA
<213> ORGANISM: Artificial Sequence
<220> FEATURE:
<223> OTHER INFORMATION: Primer

<400> SEQUENCE: 9
cgggatccat ggcgccacaa gaacaagcag tttc                              34

<210> SEQ ID NO 10
<211> LENGTH: 36
<212> TYPE: DNA
<213> ORGANISM: Artificial Sequence
<220> FEATURE:
<223> OTHER INFORMATION: Primer

<400> SEQUENCE: 10
cccaagcttt taatttgtaa ccataggaat gctatg                            36

<210> SEQ ID NO 11
<211> LENGTH: 22
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (22)..(22)
<223> OTHER INFORMATION: n is a, c, g, or t
```

<400> SEQUENCE: 11
tttttttttt tttttttttt vn                                                22

<210> SEQ ID NO 12
<211> LENGTH: 1074
<212> TYPE: DNA
<213> ORGANISM: Vitis vinifera

<400> SEQUENCE: 12

```
atggatttgg caaacggtgt gatatcagct gagctgcttc atgctcaagc tcatgtctgg      60
aatcatatat tcaacttcat aaagtctatg tcactaaaat gtgctattca actaggcatc     120
ccagacatca tccacaacca tggcaagccc atgactcttc ctgagctagt cgctaagctc     180
ccagtccacc ctaaaaggag tcagtgcgtg taccgtctca tgcgcattct tgttcattct     240
ggcttccttg ctgcgcaaag agtccaacaa ggtaaggaag aggaggggta tgtgcttaca     300
gatgcctcta ggctccttct aatggatgac tccttgagca taaggccctt ggtgcttgcc     360
atgctcgacc caatttttaac taaaccatgg cattatctga gtgcttggtt tcaaaatgat     420
gatcccactc cgttccacac tgctcatgag cggtcatttt gggattatgc cggccatgaa     480
ccccagctca caattccttt caatgaagcc atggctagcg atgctcgctt actcaccagc     540
gtgctgctta aggagggcca gggcgtattt gcggggttga actcattagt tgatgtaggg     600
ggtggcaccg gaaaagtggc caaggccatt gctaacgctt tcccacattt gaactgcacc     660
gtgttagatc tcccccacgt ggttgctggc ttgcaaggga gcaagaactt gaactacttt     720
gcaggtgata tgtttgaggc aattcctcct gcagacgcaa ttttactcaa gtggatactg     780
cacgactgga gcgatgaaga atgcgtgaag atactaaagc gatgcaggga agcaattccg     840
agcaaggaaa acggaggaaa ggtgattatc atagacatga tcatgatgaa gaatcaagga     900
gactacaagt ccacagaaac acagctgttc tttgatatga cgatgatgat tttcgccccg     960
ggtagagaga gggacgagaa cgaatgggag aagctattct tggatgctgg tttcagtcac    1020
tacaagataa ctcccatttt gggtttgagg tccctcattg aggtttatcc ttga          1074
```

<210> SEQ ID NO 13
<211> LENGTH: 357
<212> TYPE: PRT
<213> ORGANISM: Vitis vinifera

<400> SEQUENCE: 13

Met Asp Leu Ala Asn Gly Val Ile Ser Ala Glu Leu Leu His Ala Gln
1               5                  10                  15

Ala His Val Trp Asn His Ile Phe Asn Phe Ile Lys Ser Met Ser Leu
            20                  25                  30

Lys Cys Ala Ile Gln Leu Gly Ile Pro Asp Ile Ile His Asn His Gly
        35                  40                  45

Lys Pro Met Thr Leu Pro Glu Leu Val Ala Lys Leu Pro Val His Pro
    50                  55                  60

Lys Arg Ser Gln Cys Val Tyr Arg Leu Met Arg Ile Leu Val His Ser
65                  70                  75                  80

Gly Phe Leu Ala Ala Gln Arg Val Gln Gln Gly Lys Glu Glu Glu Gly
                85                  90                  95

Tyr Val Leu Thr Asp Ala Ser Arg Leu Leu Leu Met Asp Asp Ser Leu
            100                 105                 110

Ser Ile Arg Pro Leu Val Leu Ala Met Leu Asp Pro Ile Leu Thr Lys

```
                    115                 120                 125
Pro Trp His Tyr Leu Ser Ala Trp Phe Gln Asn Asp Asp Pro Thr Pro
        130                 135                 140
Phe His Thr Ala His Glu Arg Ser Phe Trp Asp Tyr Ala Gly His Glu
145                 150                 155                 160
Pro Gln Leu Asn Asn Ser Phe Asn Glu Ala Met Ala Ser Asp Ala Arg
                165                 170                 175
Leu Leu Thr Ser Val Leu Leu Lys Glu Gly Gln Gly Val Phe Ala Gly
            180                 185                 190
Leu Asn Ser Leu Val Asp Val Gly Gly Gly Thr Gly Lys Val Ala Lys
        195                 200                 205
Ala Ile Ala Asn Ala Phe Pro His Leu Asn Cys Thr Val Leu Asp Leu
    210                 215                 220
Pro His Val Val Ala Gly Leu Gln Gly Ser Lys Asn Leu Asn Tyr Phe
225                 230                 235                 240
Ala Gly Asp Met Phe Glu Ala Ile Pro Pro Ala Asp Ala Ile Leu Leu
                245                 250                 255
Lys Trp Ile Leu His Asp Trp Ser Asp Glu Glu Cys Val Lys Ile Leu
            260                 265                 270
Lys Arg Cys Arg Glu Ala Ile Pro Ser Lys Glu Asn Gly Gly Lys Val
        275                 280                 285
Ile Ile Ile Asp Met Ile Met Met Lys Asn Gln Gly Asp Tyr Lys Ser
    290                 295                 300
Thr Glu Thr Gln Leu Phe Phe Asp Met Thr Met Met Ile Phe Ala Pro
305                 310                 315                 320
Gly Arg Glu Arg Asp Glu Asn Glu Trp Glu Lys Leu Phe Leu Asp Ala
                325                 330                 335
Gly Phe Ser His Tyr Lys Ile Thr Pro Ile Leu Gly Leu Arg Ser Leu
            340                 345                 350
Ile Glu Val Tyr Pro
        355

<210> SEQ ID NO 14
<211> LENGTH: 1686
<212> TYPE: DNA
<213> ORGANISM: Arabidopsis thaliana

<400> SEQUENCE: 14
atggcgccac aagaacaagc agtttctcag gtgatggaga acagagcaa caacaacaac     60
agtgacgtca ttttccgatc aaagttaccg gatatttaca tcccgaacca cctatctctc    120
cacgactaca tcttccaaaa catctccgaa ttcgccacta agccttgcct aatcaacgga    180
ccaaccggcc acgtgtacac ttactccgac gtccacgtca tctcccgcca atcgccgcc    240
aattttcaca aactcggcgt taaccaaaac gacgtcgtca tgctcctcct cccaaactgt    300
cccgaattcg tcctctcttt cctcgccgcc tccttccgcg cgcaaccgc accgccgca    360
aaccctttct tcactccggc ggagatagct aaacaagcca agcctccaa caccaaactc    420
ataatcaccg aagctcgtta cgtcgacaaa atcaaaccac tcaaaacga cgacggagta    480
gtcatcgtct gcatcgacga caacgaatcc gtgccaatcc tgaaggctg cctccgcttc    540
accgagttga ctcagtcgac aaccgaggca tcagaagtca tcgactcggt ggagatttca    600
ccggacgacg tggtggcact acctactcc tctggcacga cgggattacc aaaaggagtg    660
atgctgactc acaagggact agtcacgagc gttgctcagc aagtcgacgg cgagaacccg    720
```

-continued

```
aatctttatt tccacagcga tgacgtcata ctctgtgttt tgcccatgtt tcatatctac      780
gctttgaact cgatcatgtt gtgtggtctt agagttggtg cggcgattct gataatgccg      840
aagtttgaga tcaatctgct attggagctg atccagaggt gtaaagtgac ggtggctccg      900
atggttccgc cgattgtgtt ggccattgcg aagtcttcgg agacggagaa gtatgatttg      960
agctcgataa gagtggtgaa atctggtgct gctcctcttg gtaaagaact tgaagatgcc     1020
gttaatgcca gtttcctaa tgccaaactc ggtcagggat acggaatgac ggaagcaggt      1080
ccagtgctag caatgtcgtt aggttttgca aaggaacctt ttccggttaa gtcaggagct     1140
tgtggtactg ttgtaagaaa tgctgagatg aaaatagttg atccagacac cggagattct     1200
ctttcgagga atcaacccgg tgagatttgt attcgtggtc accagatcat gaaaggttac     1260
ctcaacaatc cggcagctac agcagagacc attgataaag acggttggct tcatactgga     1320
gatattggat tgatcgatga cgatgacgag cttttcatcg ttgatcgatt gaagaactt      1380
atcaagtata aggttttca gtagctccg gctgagctag aggctttgct catcggtcat       1440
cctgacatta ctgatgttgc tgttgtcgca atgaaagaag aagcagctgg tgaagttcct     1500
gttgcatttg tggtgaaatc gaaggattcg gagttatcag aagatgatgt gaagcaattc     1560
gtgtcgaaac aggttgtgtt ttacaagaga atcaacaaag tgttcttcac tgaatccatt     1620
cctaaagctc catcagggaa gatattgagg aaagatctga gggcaaaact agcaaatgga     1680
ttgtga                                                                1686
```

<210> SEQ ID NO 15
<211> LENGTH: 561
<212> TYPE: PRT
<213> ORGANISM: Arabidopsis thaliana

<400> SEQUENCE: 15

```
Met Ala Pro Gln Glu Gln Ala Val Ser Gln Val Met Glu Lys Gln Ser
1               5                   10                  15

Asn Asn Asn Asn Ser Asp Val Ile Phe Arg Ser Lys Leu Pro Asp Ile
            20                  25                  30

Tyr Ile Pro Asn His Leu Ser Leu His Asp Tyr Ile Phe Gln Asn Ile
        35                  40                  45

Ser Glu Phe Ala Thr Lys Pro Cys Leu Ile Asn Gly Pro Thr Gly His
    50                  55                  60

Val Tyr Thr Tyr Ser Asp Val His Val Ile Ser Arg Gln Ile Ala Ala
65                  70                  75                  80

Asn Phe His Lys Leu Gly Val Asn Gln Asn Asp Val Val Met Leu Leu
                85                  90                  95

Leu Pro Asn Cys Pro Glu Phe Val Leu Ser Phe Leu Ala Ala Ser Phe
            100                 105                 110

Arg Gly Ala Thr Ala Thr Ala Ala Asn Pro Phe Phe Thr Pro Ala Glu
        115                 120                 125

Ile Ala Lys Gln Ala Lys Ala Ser Asn Thr Lys Leu Ile Ile Thr Glu
    130                 135                 140

Ala Arg Tyr Val Asp Lys Ile Lys Pro Leu Gln Asn Asp Asp Gly Val
145                 150                 155                 160

Val Ile Val Cys Ile Asp Asp Asn Glu Ser Val Pro Ile Pro Glu Gly
                165                 170                 175

Cys Leu Arg Phe Thr Glu Leu Thr Gln Ser Thr Thr Glu Ala Ser Glu
            180                 185                 190

Val Ile Asp Ser Val Glu Ile Ser Pro Asp Asp Val Val Ala Leu Pro
```

```
                  195                 200                 205
        Tyr Ser Ser Gly Thr Thr Gly Leu Pro Lys Gly Val Met Leu Thr His
            210                 215                 220

Lys Gly Leu Val Thr Ser Val Ala Gln Gln Val Asp Gly Glu Asn Pro
        225                 230                 235                 240

Asn Leu Tyr Phe His Ser Asp Asp Val Ile Leu Cys Val Leu Pro Met
                        245                 250                 255

Phe His Ile Tyr Ala Leu Asn Ser Ile Met Leu Cys Gly Leu Arg Val
                    260                 265                 270

Gly Ala Ala Ile Leu Ile Met Pro Lys Phe Glu Ile Asn Leu Leu Leu
                275                 280                 285

Glu Leu Ile Gln Arg Cys Lys Val Thr Val Ala Pro Met Val Pro Pro
        290                 295                 300

Ile Val Leu Ala Ile Ala Lys Ser Ser Glu Thr Glu Lys Tyr Asp Leu
        305                 310                 315                 320

Ser Ser Ile Arg Val Val Lys Ser Gly Ala Ala Pro Leu Gly Lys Glu
                        325                 330                 335

Leu Glu Asp Ala Val Asn Ala Lys Phe Pro Asn Ala Lys Leu Gly Gln
                    340                 345                 350

Gly Tyr Gly Met Thr Glu Ala Gly Pro Val Leu Ala Met Ser Leu Gly
                355                 360                 365

Phe Ala Lys Glu Pro Phe Pro Val Lys Ser Gly Ala Cys Gly Thr Val
        370                 375                 380

Val Arg Asn Ala Glu Met Lys Ile Val Asp Pro Asp Thr Gly Asp Ser
        385                 390                 395                 400

Leu Ser Arg Asn Gln Pro Gly Glu Ile Cys Ile Arg Gly His Gln Ile
                        405                 410                 415

Met Lys Gly Tyr Leu Asn Asn Pro Ala Ala Thr Ala Glu Thr Ile Asp
                    420                 425                 430

Lys Asp Gly Trp Leu His Thr Gly Asp Ile Gly Leu Ile Asp Asp Asp
                435                 440                 445

Asp Glu Leu Phe Ile Val Asp Arg Leu Lys Glu Leu Ile Lys Tyr Lys
        450                 455                 460

Gly Phe Gln Val Ala Pro Ala Glu Leu Glu Ala Leu Leu Ile Gly His
        465                 470                 475                 480

Pro Asp Ile Thr Asp Val Ala Val Val Ala Met Lys Glu Glu Ala Ala
                        485                 490                 495

Gly Glu Val Pro Val Ala Phe Val Val Lys Ser Lys Asp Ser Glu Leu
                    500                 505                 510

Ser Glu Asp Asp Val Lys Gln Phe Val Ser Lys Gln Val Val Phe Tyr
                515                 520                 525

Lys Arg Ile Asn Lys Val Phe Phe Thr Glu Ser Ile Pro Lys Ala Pro
        530                 535                 540

Ser Gly Lys Ile Leu Arg Lys Asp Leu Arg Ala Lys Leu Ala Asn Gly
        545                 550                 555                 560

Leu

<210> SEQ ID NO 16
<211> LENGTH: 1179
<212> TYPE: DNA
<213> ORGANISM: Vitis vinifera

<400> SEQUENCE: 16
atggcttcag tcgaggaatt tagaaacgct caacgtgcca agggtccggc caccatccta    60
```

-continued

```
gccattggca cagctacccc cgaccactgt gtctaccagt ctgattatgc tgattactat    120
ttcaaggtca ctaagagcga gcacatgact gcgttgaaga agaagttcaa tcgcatatgt    180
gacaaatcca tgatcaagaa gcgttacatt catttgaccg aagaaatgct tgaggagcac    240
ccaaacattg gtgcttatat ggctccatct cttaacatac gccaagagat tatcactgct    300
gaggtaccca agctcggtaa ggaagcagca ttgaaggctc ttaaagagtg gggtcagcct    360
aaatcgaaga tcacccacct tgtatttttgt accacctcag gtgtagaaat gcctggtgca    420
gattataaac tcgctaatct tttaggcctc gaaccatctg tcagaagagt gatgttgtac    480
catcaagggt gctatgcagg tggaactgtc cttcgaaccg ctaaggatct tgcagagaat    540
aatgcaggag cacgagttct tgtggtgtgc tctgagatca cagttgttac atttcgcggc    600
ccttccgaag atgctttgga ctctttagtt ggccaagccc ttttggtga tggttctgca     660
gctgtaatcg taggatcaga tccggatatc tcaattgaac gaccactctt ccagcttgtc    720
tcagcagccc aaacatttat tcctaattct gcaggtgcca ttgcaggaaa cttacgtgag    780
gtgggactca cctttcattt gtggcccaat gtgcccactt taatttctga aacgtagag     840
aaatgtttga ctcaggcttt tgacccactt ggtattagcg attggaactc gttatttgg     900
attgctcacc caggtggccc tgcaattctt gatgcagttg aagcaaaact caatttagat    960
aaaaagaaac tcgaagcaac gaggcatgtg ttaagtgagt atggaaacat gtcaagtgca   1020
tgtgtgttgt ttattttgga tgagatgaga agaaatccc ttaaggggga gagggccacc    1080
acgggtgaag gattggattg gggagtatta ttcggttttg gaccaggctt gactattgaa   1140
actgttgtgt tgcatagcat tcctatggtt acaaattaa                          1179
```

<210> SEQ ID NO 17
<211> LENGTH: 392
<212> TYPE: PRT
<213> ORGANISM: Vitis vinifera

<400> SEQUENCE: 17

```
Met Ala Ser Val Glu Glu Phe Arg Asn Ala Gln Arg Ala Lys Gly Pro
1               5                   10                  15

Ala Thr Ile Leu Ala Ile Gly Thr Ala Thr Pro Asp His Cys Val Tyr
            20                  25                  30

Gln Ser Asp Tyr Ala Asp Tyr Tyr Phe Lys Val Thr Lys Ser Glu His
        35                  40                  45

Met Thr Ala Leu Lys Lys Lys Phe Asn Arg Ile Cys Asp Lys Ser Met
    50                  55                  60

Ile Lys Lys Arg Tyr Ile His Leu Thr Glu Glu Met Leu Glu Glu His
65                  70                  75                  80

Pro Asn Ile Gly Ala Tyr Met Ala Pro Ser Leu Asn Ile Arg Gln Glu
                85                  90                  95

Ile Ile Thr Ala Glu Val Pro Lys Leu Gly Lys Glu Ala Ala Leu Lys
            100                 105                 110

Ala Leu Lys Glu Trp Gly Gln Pro Lys Ser Lys Ile Thr His Leu Val
        115                 120                 125

Phe Cys Thr Thr Ser Gly Val Glu Met Pro Gly Ala Asp Tyr Lys Leu
    130                 135                 140

Ala Asn Leu Leu Gly Leu Glu Pro Ser Val Arg Arg Val Met Leu Tyr
145                 150                 155                 160

His Gln Gly Cys Tyr Ala Gly Gly Thr Val Leu Arg Thr Ala Lys Asp
                165                 170                 175
```

Leu Ala Glu Asn Asn Ala Gly Ala Arg Val Leu Val Val Cys Ser Glu
            180                 185                 190
Ile Thr Val Val Thr Phe Arg Gly Pro Ser Glu Asp Ala Leu Asp Ser
        195                 200                 205
Leu Val Gly Gln Ala Leu Phe Gly Asp Gly Ser Ala Ala Val Ile Val
    210                 215                 220
Gly Ser Asp Pro Asp Ile Ser Ile Glu Arg Pro Leu Phe Gln Leu Val
225                 230                 235                 240
Ser Ala Ala Gln Thr Phe Ile Pro Asn Ser Ala Gly Ala Ile Ala Gly
                245                 250                 255
Asn Leu Arg Glu Val Gly Leu Thr Phe His Leu Trp Pro Asn Val Pro
            260                 265                 270
Thr Leu Ile Ser Glu Asn Val Glu Lys Cys Leu Thr Gln Ala Phe Asp
        275                 280                 285
Pro Leu Gly Ile Ser Asp Trp Asn Ser Leu Phe Trp Ile Ala His Pro
    290                 295                 300
Gly Gly Pro Ala Ile Leu Asp Ala Val Glu Ala Lys Leu Asn Leu Asp
305                 310                 315                 320
Lys Lys Lys Leu Glu Ala Thr Arg His Val Leu Ser Glu Tyr Gly Asn
                325                 330                 335
Met Ser Ser Ala Cys Val Leu Phe Ile Leu Asp Glu Met Arg Lys Lys
            340                 345                 350
Ser Leu Lys Gly Glu Arg Ala Thr Thr Gly Glu Gly Leu Asp Trp Gly
        355                 360                 365
Val Leu Phe Gly Phe Gly Pro Gly Leu Thr Ile Glu Thr Val Val Leu
    370                 375                 380
His Ser Ile Pro Met Val Thr Asn
385                 390

<210> SEQ ID NO 18
<211> LENGTH: 2871
<212> TYPE: DNA
<213> ORGANISM: Artificial Sequence
<220> FEATURE:
<223> OTHER INFORMATION: fusion gene

<400> SEQUENCE: 18
atggcgccac aagaacaagc agtttctcag gtgatggaga acagagcaa caacaacaac      60 agtgacgtca ttttccgatc aaagttaccg gatatttaca tcccgaacca cctatctctc     120
cacgactaca tcttccaaaa catctccgaa ttcgccacta gccttgcct aatcaacgga      180 ccaaccggcc acgtgtacac ttactccgac gtccacgtca tctcccgcca atcgccgcc     240 aattttcaca actcggcgt taaccaaaac gacgtcgtca tgctcctcct cccaaactgt     300
cccgaattcg tcctctcttt cctcgccgcc tccttccgcg cgcaaccgc caccgccgca     360 aacccttttct tcactccggc ggagatagct aaacaagcca agcctccaa caccaaactc     420 ataatcaccg aagctcgtta cgtcgacaaa atcaaaccac ttcaaaacga cgacggagta     480
gtcatcgtct gcatcgacga caacgaatcg tgccaatcc tgaaggctg cctccgcttc     540 accgagttga ctcagtcgac aaccgaggca tcagaagtca tcgactcggt ggagatttca     600
ccggacgacg tggtggcact accttactcc tctggcacga cgggattacc aaaaggagtg     660
atgctgactc acaagggact agtcacgagc gttgctcagc aagtcgacgg cgagaacccg     720
aatctttatt tccacagcga tgacgtcata ctctgtgttt tgcccatgtt tcatatctac     780

```
gctttgaact cgatcatgtt gtgtggtctt agagttggtg cggcgattct gataatgccg    840
aagtttgaga tcaatctgct attggagctg atccagaggt gtaaagtgac ggtggctccg    900
atggttccgc cgattgtgtt ggccattgcg aagtcttcgg agacggagaa gtatgatttg    960
agctcgataa gagtggtgaa atctggtgct gctcctcttg gtaaagaact tgaagatgcc   1020
gttaatgcca gtttcctaa tgccaaactc ggtcaggat acggaatgac ggaagcaggt    1080
ccagtgctag caatgtcgtt aggttttgca aggaaccctt ttccggttaa gtcaggagct   1140
tgtggtactg ttgtaagaaa tgctgagatg aaaatagttg atccagacac cggagattct   1200
ctttcgagga atcaacccgg tgagatttgt attcgtggtc accagatcat gaaaggttac   1260
ctcaacaatc cggcagctac agcagagacc attgataaag acggttggct tcatactgga   1320
gatattggat tgatcgatga cgatgacgag ctttttcatcg ttgatcgatt gaaagaactt   1380
atcaagtata aggttttca ggtagctccg gctgagctag aggctttgct catcggtcat   1440
cctgacatta ctgatgttgc tgttgtcgca atgaaagaag aagcagctgg tgaagttcct   1500
gttgcatttg tggtgaaatc gaaggattcg gagttatcag aagatgatgt gaagcaattc   1560
gtgtcgaaac aggttgtgtt ttacaagaga atcaacaaag tgttcttcac tgaatccatt   1620
cctaaagctc atcagggaa gatattgagg aaagatctga gggcaaaact agcaaatgga   1680
ttgggatctg gcatggcttc agtcgaggaa tttagaaacg ctcaacgtgc aagggtccg    1740
gccaccatcc tagccattgg cacagctacc cccgaccact gtgtctacca gtctgattat   1800
gctgattact atttcaaggt cactaagagc gagcacatga ctgcgttgaa gaagaagttc   1860
aatcgcatat gtgacaaatc catgatcaag aagcgttaca ttcatttgac cgaagaaatg   1920
cttgaggagc acccaaacat tggtgcttat atggctccat ctcttaacat acgccaagag   1980
attatcactg ctgaggtacc caagctcggt aaggaagcag cattgaaggc tcttaaagag   2040
tggggtcagc ctaaatcgaa gatcacccac cttgtatttt gtaccacctc aggtgtagaa   2100
atgcctggtg cagattataa actcgctaat cttttaggcc tcgaaccatc tgtcagaaga   2160
gtgatgttgt accatcaagg gtgctatgca ggtggaactg tccttcgaac cgctaaggat   2220
cttgcagaga taatgcagg agcacgagtt cttgtggtgt gctctgagat cacagttgtt   2280
acatttcgcg gcccttccga agatgctttg gactctttag ttggccaagc cctttttggt   2340
gatggttctg cagctgtaat cgtaggatca gatccggata tctcaattga acgaccactc   2400
ttccagcttg tctcagcagc ccaaacattt attcctaatt ctgcaggtgc cattgcagga   2460
aacttacgtg aggtgggact caccttttcat ttgtggccca atgtgcccac tttaatttct   2520
gagaacgtag agaaatgttt gactcaggct tttgacccac ttggtattag cgattggaac   2580
tcgttatttt ggattgctca cccaggtggc cctgcaattc ttgatgcagt tgaagcaaaa   2640
ctcaatttag ataaaaagaa actcgaagca acgaggcatg tgttaagtga gtatggaaac   2700
atgtcaagtg catgtgtgtt gtttatttt gatgagatga gaagaaatc ccttaagggg   2760
gagagggcca ccacgggtga aggattggat tggggagtat tattcggttt tggaccaggc   2820
ttgactattg aaactgttgt gttgcatagc attcctatgg ttacaaatta a            2871
```

<210> SEQ ID NO 19
<211> LENGTH: 956
<212> TYPE: PRT
<213> ORGANISM: Artificial Sequence
<220> FEATURE:
<223> OTHER INFORMATION: fusion protein

<400> SEQUENCE: 19

```
Met Ala Pro Gln Glu Gln Ala Val Ser Gln Val Met Glu Lys Gln Ser
1               5                   10                  15

Asn Asn Asn Asn Ser Asp Val Ile Phe Arg Ser Lys Leu Pro Asp Ile
            20                  25                  30

Tyr Ile Pro Asn His Leu Ser Leu His Asp Tyr Ile Phe Gln Asn Ile
        35                  40                  45

Ser Glu Phe Ala Thr Lys Pro Cys Leu Ile Asn Gly Pro Thr Gly His
    50                  55                  60

Val Tyr Thr Tyr Ser Asp Val His Val Ile Ser Arg Gln Ile Ala Ala
65                  70                  75                  80

Asn Phe His Lys Leu Gly Val Asn Gln Asn Asp Val Val Met Leu Leu
                85                  90                  95

Leu Pro Asn Cys Pro Glu Phe Val Leu Ser Phe Leu Ala Ala Ser Phe
            100                 105                 110

Arg Gly Ala Thr Ala Thr Ala Ala Asn Pro Phe Phe Thr Pro Ala Glu
            115                 120                 125

Ile Ala Lys Gln Ala Lys Ala Ser Asn Thr Lys Leu Ile Ile Thr Glu
        130                 135                 140

Ala Arg Tyr Val Asp Lys Ile Lys Pro Leu Gln Asn Asp Asp Gly Val
145                 150                 155                 160

Val Ile Val Cys Ile Asp Asp Asn Glu Ser Val Pro Ile Pro Glu Gly
                165                 170                 175

Cys Leu Arg Phe Thr Glu Leu Thr Gln Ser Thr Thr Glu Ala Ser Glu
            180                 185                 190

Val Ile Asp Ser Val Glu Ile Ser Pro Asp Asp Val Val Ala Leu Pro
        195                 200                 205

Tyr Ser Ser Gly Thr Thr Gly Leu Pro Lys Gly Val Met Leu Thr His
210                 215                 220

Lys Gly Leu Val Thr Ser Val Ala Gln Gln Val Asp Gly Glu Asn Pro
225                 230                 235                 240

Asn Leu Tyr Phe His Ser Asp Asp Val Ile Leu Cys Val Leu Pro Met
            245                 250                 255

Phe His Ile Tyr Ala Leu Asn Ser Ile Met Leu Cys Gly Leu Arg Val
            260                 265                 270

Gly Ala Ala Ile Leu Ile Met Pro Lys Phe Glu Ile Asn Leu Leu Leu
        275                 280                 285

Glu Leu Ile Gln Arg Cys Lys Val Thr Val Ala Pro Met Val Pro Pro
290                 295                 300

Ile Val Leu Ala Ile Ala Lys Ser Ser Glu Thr Glu Lys Tyr Asp Leu
305                 310                 315                 320

Ser Ser Ile Arg Val Val Lys Ser Gly Ala Ala Pro Leu Gly Lys Glu
            325                 330                 335

Leu Glu Asp Ala Val Asn Ala Lys Phe Pro Asn Ala Lys Leu Gly Gln
            340                 345                 350

Gly Tyr Gly Met Thr Glu Ala Gly Pro Val Leu Ala Met Ser Leu Gly
        355                 360                 365

Phe Ala Lys Glu Pro Phe Pro Val Lys Ser Gly Ala Cys Gly Thr Val
        370                 375                 380

Val Arg Asn Ala Glu Met Lys Ile Val Asp Pro Asp Thr Gly Asp Ser
385                 390                 395                 400

Leu Ser Arg Asn Gln Pro Gly Glu Ile Cys Ile Arg Gly His Gln Ile
            405                 410                 415
```

```
Met Lys Gly Tyr Leu Asn Asn Pro Ala Ala Thr Ala Glu Thr Ile Asp
                420                 425                 430

Lys Asp Gly Trp Leu His Thr Gly Asp Ile Gly Leu Ile Asp Asp Asp
            435                 440                 445

Asp Glu Leu Phe Ile Val Asp Arg Leu Lys Glu Leu Ile Lys Tyr Lys
        450                 455                 460

Gly Phe Gln Val Ala Pro Ala Glu Leu Glu Ala Leu Leu Ile Gly His
465                 470                 475                 480

Pro Asp Ile Thr Asp Val Ala Val Val Ala Met Lys Glu Glu Ala Ala
                485                 490                 495

Gly Glu Val Pro Val Ala Phe Val Val Lys Ser Lys Asp Ser Glu Leu
            500                 505                 510

Ser Glu Asp Asp Val Lys Gln Phe Val Ser Lys Gln Val Val Phe Tyr
        515                 520                 525

Lys Arg Ile Asn Lys Val Phe Phe Thr Glu Ser Ile Pro Lys Ala Pro
530                 535                 540

Ser Gly Lys Ile Leu Arg Lys Asp Leu Arg Ala Lys Leu Ala Asn Gly
545                 550                 555                 560

Leu Gly Ser Gly Met Ala Ser Val Glu Glu Phe Arg Asn Ala Gln Arg
                565                 570                 575

Ala Lys Gly Pro Ala Thr Ile Leu Ala Ile Gly Thr Ala Thr Pro Asp
            580                 585                 590

His Cys Val Tyr Gln Ser Asp Tyr Ala Asp Tyr Tyr Phe Lys Val Thr
        595                 600                 605

Lys Ser Glu His Met Thr Ala Leu Lys Lys Phe Asn Arg Ile Cys
610                 615                 620

Asp Lys Ser Met Ile Lys Lys Arg Tyr Ile His Leu Thr Glu Glu Met
625                 630                 635                 640

Leu Glu Glu His Pro Asn Ile Gly Ala Tyr Met Ala Pro Ser Leu Asn
                645                 650                 655

Ile Arg Gln Glu Ile Ile Thr Ala Glu Val Pro Lys Leu Gly Lys Glu
            660                 665                 670

Ala Ala Leu Lys Ala Leu Lys Glu Trp Gly Gln Pro Lys Ser Lys Ile
        675                 680                 685

Thr His Leu Val Phe Cys Thr Thr Ser Gly Val Glu Met Pro Gly Ala
    690                 695                 700

Asp Tyr Lys Leu Ala Asn Leu Leu Gly Leu Glu Pro Ser Val Arg Arg
705                 710                 715                 720

Val Met Leu Tyr His Gln Gly Cys Tyr Ala Gly Gly Thr Val Leu Arg
                725                 730                 735

Thr Ala Lys Asp Leu Ala Glu Asn Asn Ala Gly Ala Arg Val Leu Val
            740                 745                 750

Val Cys Ser Glu Ile Thr Val Val Thr Phe Arg Gly Pro Ser Glu Asp
        755                 760                 765

Ala Leu Asp Ser Leu Val Gly Gln Ala Leu Phe Gly Asp Gly Ser Ala
    770                 775                 780

Ala Val Ile Val Gly Ser Asp Pro Asp Ile Ser Ile Glu Arg Pro Leu
785                 790                 795                 800

Phe Gln Leu Val Ser Ala Ala Gln Thr Phe Ile Pro Asn Ser Ala Gly
                805                 810                 815

Ala Ile Ala Gly Asn Leu Arg Glu Val Gly Leu Thr Phe His Leu Trp
            820                 825                 830

Pro Asn Val Pro Thr Leu Ile Ser Glu Asn Val Glu Lys Cys Leu Thr
```

-continued

```
                835                 840                 845
Gln Ala Phe Asp Pro Leu Gly Ile Ser Asp Trp Asn Ser Leu Phe Trp
        850                 855                 860

Ile Ala His Pro Gly Gly Pro Ala Ile Leu Asp Ala Val Glu Ala Lys
865                 870                 875                 880

Leu Asn Leu Asp Lys Lys Leu Glu Ala Thr Arg His Val Leu Ser
                885                 890                 895

Glu Tyr Gly Asn Met Ser Ser Ala Cys Val Leu Phe Ile Leu Asp Glu
            900                 905                 910

Met Arg Lys Lys Ser Leu Lys Gly Glu Arg Ala Thr Thr Gly Glu Gly
        915                 920                 925

Leu Asp Trp Gly Val Leu Phe Gly Phe Gly Pro Gly Leu Thr Ile Glu
    930                 935                 940

Thr Val Val Leu His Ser Ile Pro Met Val Thr Asn
945                 950                 955
```